US012678535B2

(12) United States Patent
Hall et al.

(10) Patent No.: US 12,678,535 B2
(45) Date of Patent: Jul. 14, 2026

(54) MULTILAYER VASCULAR GRAFT

(71) Applicant: Merit Medical Systems, Inc., South Jordan, UT (US)

(72) Inventors: John Hall, Bountiful, UT (US); Wayne Mower, Bountiful, UT (US); Doug Friedrichs, Salt Lake City, UT (US); Lucia Irazabal, Holladay, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 91 days.

(21) Appl. No.: 17/195,350

(22) Filed: Mar. 8, 2021

(65) Prior Publication Data

US 2021/0283302 A1    Sep. 16, 2021

Related U.S. Application Data

(60) Provisional application No. 62/987,478, filed on Mar. 10, 2020.

(51) Int. Cl.
*A61L 27/16*      (2006.01)
*A61L 27/26*      (2006.01)
*A61L 27/56*      (2006.01)

(52) U.S. Cl.
CPC ............... *A61L 27/16* (2013.01); *A61L 27/26* (2013.01); *A61L 27/56* (2013.01)

(58) Field of Classification Search
CPC ........... A61L 27/16; A61L 27/56; A61L 27/26
See application file for complete search history.

(56) References Cited

U.S. PATENT DOCUMENTS

| | | | | |
|---|---|---|---|---|
| 2003/0144725 A1* | 7/2003 | Lombardi | ................. | A61F 2/07 623/1.13 |
| 2005/0165476 A1* | 7/2005 | Furst | ......................... | A61F 2/06 623/1.42 |
| 2008/0208325 A1* | 8/2008 | Helmus | ..................... | A61F 2/06 623/1.13 |
| 2009/0182404 A1* | 7/2009 | Shokoohi | .................. | A61F 2/90 623/1.42 |
| 2010/0179642 A1* | 7/2010 | Bogert | .................... | A61L 27/16 623/1.3 |
| 2012/0111489 A1 | 5/2012 | Weinberg | | |

FOREIGN PATENT DOCUMENTS

JP          04253856        9/1992

OTHER PUBLICATIONS https://www.applerubber.com/src/pdf/section6-material-selection-guide.pdf (Year: 2023).*
https://www.polyglobal.co.uk/a-guide-to-shore-hardness/ (Year: 2023).*
JPH04253856A Description (Year: 1991).*
JPH04253856A Drawings (Year: 1991).*
https://www.bearingworks.com/uploaded-assets/pdfs/retainers/ptfe-datasheet.pdf (Year: 2024).*
Hardness Comparison of Polymer Specimens Produced with Different Processes, Vian et al., 2018 (Year: 2018).*
International Search Report and Written Opinion dated Jun. 29, 2021 for PCT/US2021/021380.
European Search Report dated Mar. 7, 2024 for EP21768813.4.
European Search Report dated Mar. 25, 2025 for EP21768813.4.

* cited by examiner

*Primary Examiner* — Andrew S Rosenthal
*Assistant Examiner* — Danielle Kim
(74) *Attorney, Agent, or Firm* — Dorsey & Whitney LLP

(57) ABSTRACT

Devices used to provide vascular access, methods of manufacture, and methods of use are disclosed. The devices may be a vascular graft having a wall configured to seal following repeated punctures with a needle. The wall may include a plurality of layers of differing materials. The wall may also include a bead configured to prevent kinking of the vascular graft. The bead may be spirally wrapped around the vascular graft or be discrete C-shaped beads that provide a gap for needle access.

18 Claims, 8 Drawing Sheets

MULTILAYER VASCULAR GRAFT

RELATED APPLICATIONS

The present application claims priority to U.S. Provisional Application No. 62/987,478, filed on Mar. 10, 2020 and titled, "Multilayer Vascular Graft," which is hereby incorporated by reference in its entirety.

TECHNICAL FIELD

The present disclosure relates generally to devices used to provide vascular access, includes devices configured to provide vascular access for hemodialysis patients. More specifically, in some embodiments, the present disclosure relates to a puncturable artificial vascular graft.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
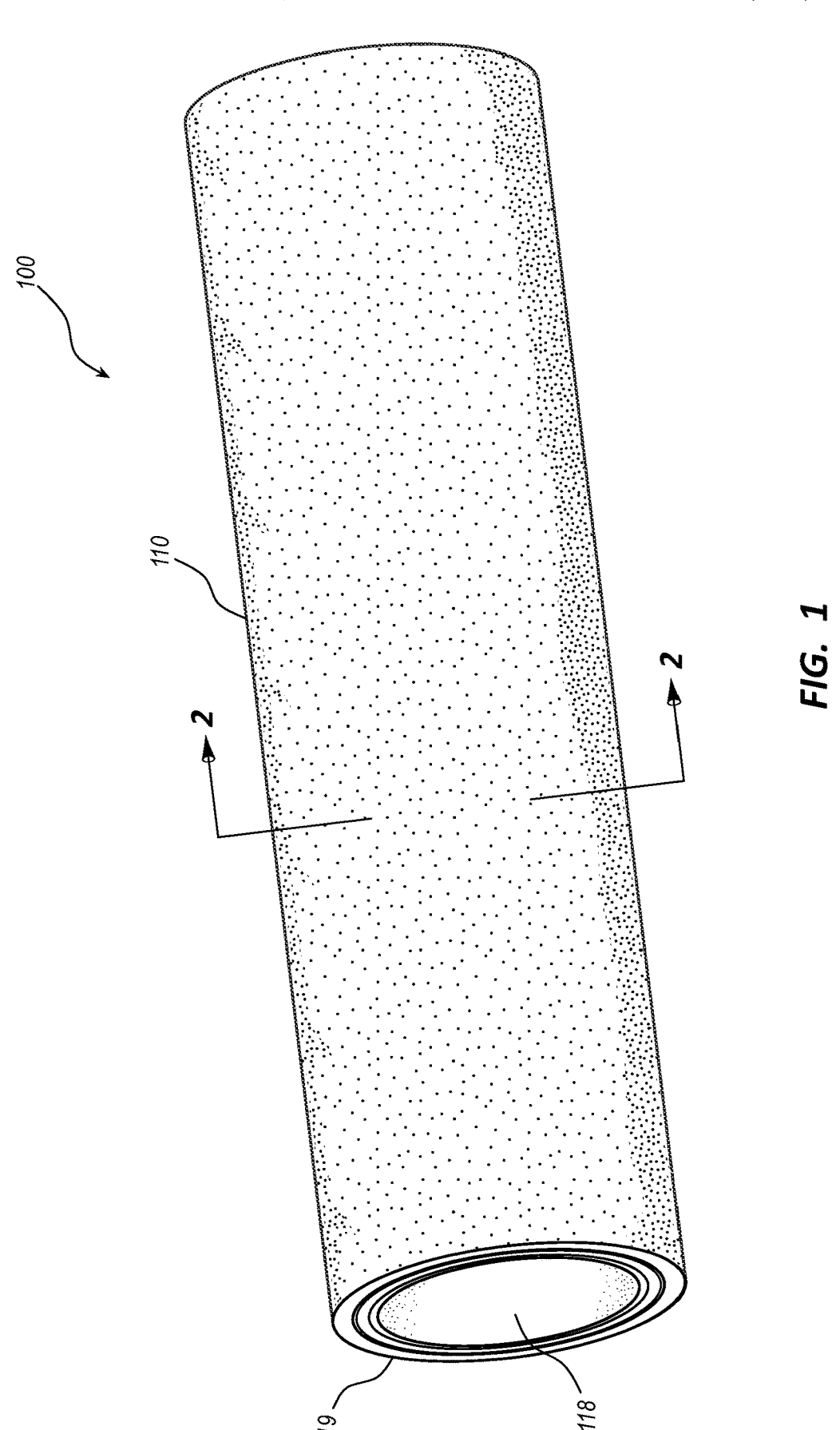
FIG. 1 is a perspective view of an embodiment of a vascular graft.

Vascular access may be part of various hemodialysis treatment procedures. In some instances, such vascular access may be facilitated by an arteriovenous fistula formed from connecting the patient's own artery to a vein, by a hemodialysis catheter inserted into a central vein, or by an artificial vascular graft connecting the patient's artery to a vein.

In some embodiments, vascular grafts within the scope of this disclosure may include a body, including bodies with a tubular or generally tubular form. Further, the body may include a wall comprising multiple layers or may be comprised of a single layer. In certain multilayer embodiments, the wall may comprise an inner layer, an intermediate layer, a tie layer, and an outer layer. In various embodiments, any of these layers may be omitted and/or other layers may also be included. In some embodiments, the inner layer may be a sleeve formed from a first polymer, the intermediate layer may be disposed over the inner layer and may comprise a sprayed layer of a second polymer, the tie layer may be disposed over the intermediate layer and may be a third polymer, and the outer layer may be a sleeve formed of a fourth polymer and may comprise a porous structure. The tie layer and the outer layer may form a laminate.

In certain instances, a bead may be disposed within the tie layer and extend over at least a portion of a length of the body. The bead may comprise a spiral or helix that extends around a circumference of the vascular graft and along a length thereof. The bead may also comprise discrete rings extending around a circumference of the vascular graft and spaced along a length thereof. Furthermore, embodiments wherein the bead extends only around a partial circumference of the vascular graft are within the scope of this disclosure. For example, a bead that follows a spiral or helical path may be discontinuous, such that it comprises spaces along the helical path. These spaces may be aligned at a circumferential position along a length of the vascular graft, creating a gap running longitudinally along a portion of the length of the vascular graft. In other instances, the bead may be comprised of partial circular members. The partial circular members may be spaced along at least a portion of the length of the body. The partial circular members may be positioned such they define a gap disposed between ends of the partial circular members. Thus, the gap may be positioned at a particular circumferential position and extend along a longitudinal length of the vascular graft. In any embodiment comprising such a gap, a thickness of the wall at the gap may be thinner than a thickness at the partial circular members.

In some instances, the vascular graft may be used in connection with a hemodialysis treatment for a patient. For example, the vascular graft may initially be implanted in a patient such that it is coupled to an artery at one end and a vein at an opposite end and used to shunt the patient's blood from the artery to the vein. During subsequent treatments, the vascular graft may be punctured with an access device, such as a needle, to provide vascular access for a hemodialysis treatment. Such treatments may be performed repeatedly over an extended time period, such as weeks, months, or longer. Thus, the graft may be repeatedly punctured over this extended time interval. During each treatment, the patient's blood may be drawn out of the vascular graft through a first access device and returned to the vascular graft through a second access device following filtration of the blood. Upon removal of the access devices, puncture sites in the wall of the vascular graft may be configured to close and seal to prevent leakage of blood into surrounding tissue.

In embodiments where the vascular graft comprises a gap between portions of a bead, the vascular graft may be configured to be punctured in or adjacent the gap.

As part of some treatments, the vascular graft may be used to bypass a blockage in a patient's vessel in an extremity, such as a leg. An end of the vascular graft may be coupled to the vessel proximal to the blockage and an opposite end coupled to the vessel distal to the blockage. Blood may thus flow through the vascular graft to supply a lower extremity with blood.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

FIGS. 1-8 illustrate different views of vascular grafts and related components. In certain views each vascular graft may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

Figure 2:
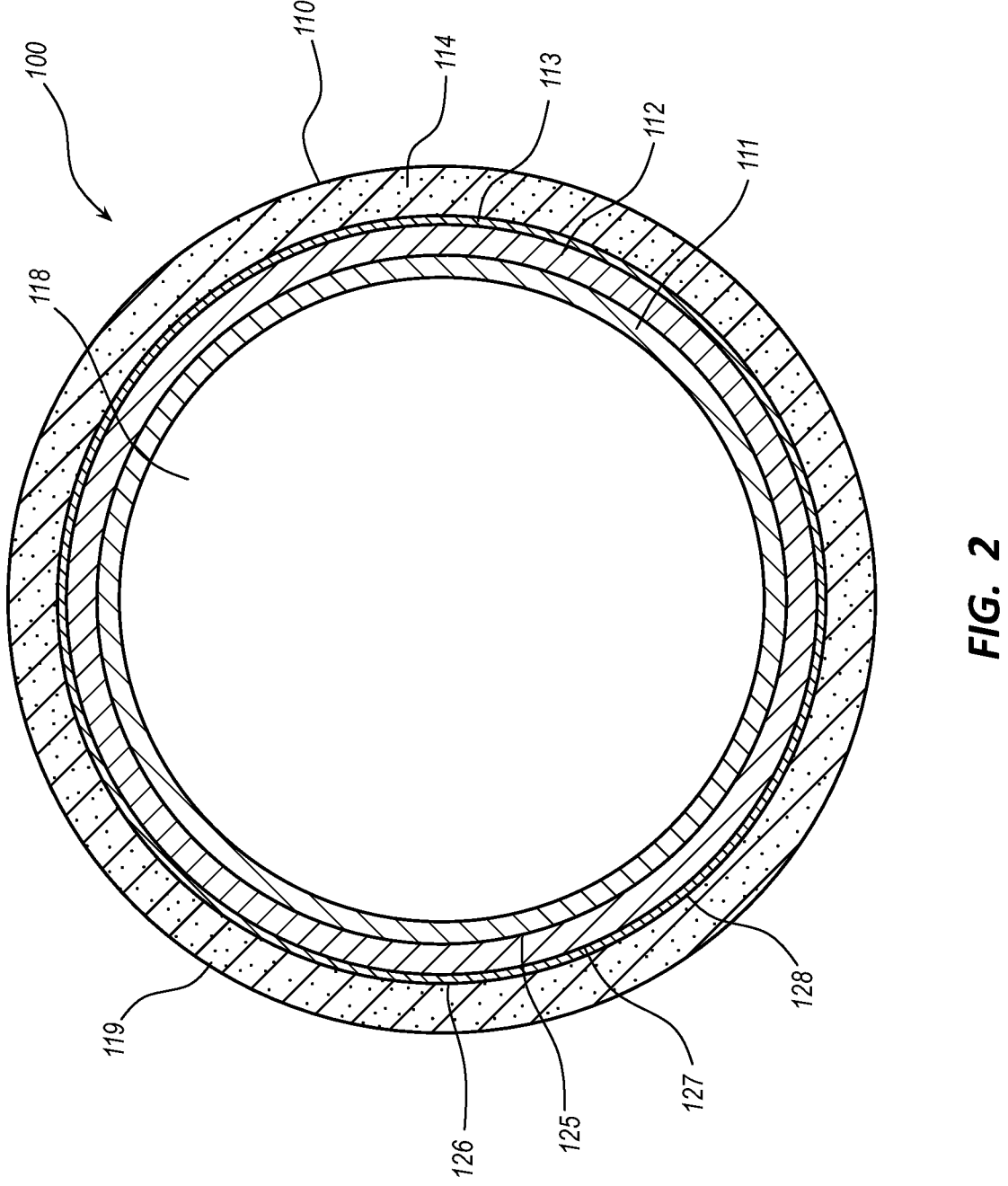
FIG. 2 is a transverse cross-sectional view of the vascular graft of FIG. 1, taken through plane 2-2 of FIG. 1.

FIGS. 1-2 depict an embodiment of a vascular graft 100. As depicted, the vascular graft 100 may include a body 110. The body 110 may include a tubular form having a wall 119 and a bore 118. A transverse cross-section of the body 110 may be circular or annular shaped as shown in FIG. 2. In other embodiments, the transverse cross-section of the body 110 may be of any suitable shape, such as an oval, lens, semicircle, ellipse, etc. In some embodiments, a length of the body 110 may range from about 5 cm to about 80 cm. The bore 118 may extend through the length of the body 110, from a proximal end of the body 110 to a distal end of the body 110. In some embodiments, the bore may have a diameter ranging from about 3 mm to about 22 mm, from about 4 mm to about 10 mm, and from about 5 mm to about 8 mm. In some embodiments, an end of the body 110 may be tapered such that the bore diameter is smaller adjacent the end than the bore diameter adjacent a medial portion of the body 110. For example, the bore diameter adjacent the end of the body 110 may be about four mm and the bore diameter adjacent the medial portion may be about six mm to seven mm. Embodiments wherein both the proximal and distal ends are tapered, only one end is tapered, and embodiment wherein neither end is tapered are within the scope of this disclosure.

The wall 119 may be formed of multiple layers. In the illustrated embodiment of FIG. 2, the wall 119 comprises four layers. Walls have more or fewer layers are within the scope of this disclosure. For example, in some embodiments, the wall 119 may comprise two, three, five, six, or more layers. As depicted, the wall 119 comprises an inner layer or sleeve 111, an intermediate layer 112, a tie layer 113, and an outer layer or sleeve 114. Any of these layers may be comprised of one or more sublayers, including embodiments wherein sublayers of the enumerated layers outlined above are comprised of different materials. For example, a layer such as the inner sleeve 111 may comprise an extruded silicone sleeve with a porous ePTFE layer coupled to its inner diameter, wherein the combination of the extruded silicone sleeve and the porous ePTFE are collectively referred to as comprising the inner sleeve 111.

In some embodiments, the inner sleeve 111 may be an extruded tube. The inner sleeve 111 may be formed from any suitable material, including materials configured to provide durability and support during manufacture of the vascular graft 100. In some embodiments, the inner sleeve 111 may be comprised of a first polymer material, for example, silicone. In other embodiments, the inner sleeve 111 may include any suitable material, such as polyurethanes, fluoroelastomers, thermal plastic elastomers, etc. Furthermore, in some embodiments, the inner sleeve 111 may comprise a fibrous polytetrafluoroethylene (PTFE) film. Fibrous PTFE film layers within the scope of this disclosure include expanded PTFE (ePTFE) layers and layers formed by rotational spinning or electrospinning a PTFE dispersion through an orifice to form fibers and collecting spun fibers on a mandrel to create an electrospun or rotational spun fibrous layer. As noted above, the inner sleeve 111 may collectively comprise an extruded silicone layer coupled to a porous PTFE layer. A hardness of the first polymer may range from about 5 A to about 80 A, from about 40 A to about 60 A, and may be about 50 A on a Shore A hardness scale. A thickness of the inner sleeve 111 may range from about 40 μm to about 350 μm, from about 100 μm to about 250 μm and be about 200 μm. In some embodiments, the inner sleeve 111 may also include additives. For example, the additives may be radiopaque agents, antimicrobial agents, antithrombogenic agents, etc. The inner sleeve 111 may be configured as the innermost layer of the wall and, thus, may be configured as the blood contacting layer of the vascular graft 100.

The intermediate layer 112 may be disposed over the inner sleeve 111 such that the intermediate layer 112 covers a full length of the inner sleeve 111. The intermediate layer 112 may include a second polymer that is different than the first polymer of the inner sleeve 111. The second polymer and the first polymer may also comprise different formulations of similar materials, such as two types of silicone with different hardnesses or other properties. Thus, in certain embodiments, the second polymer of the intermediate layer 112 may be silicone. In other embodiments, the second polymer of the intermediate layer 112 may be any suitable material, such as polyurethane, fluoroelastomer, thermal plastic elastomer, etc. The second polymer may have a hardness that is less than the hardness of the first silicone polymer of the inner sleeve 111. A hardness of the second polymer of the intermediate layer 112 may range from about 5 A to about 80 A, from about 15 A to about 40 A and may be about 25 A on a Shore A hardness scale. The second polymer may be applied to the inner sleeve 111 using a spraying technique where a dispersion of the second polymer and a solvent is aerosolized or atomized, including embodiments wherein a dispersion of the second polymer and a solvent is aerosolized and sprayed onto the inner sleeve 111. In some embodiments, the second polymer may be applied to the inner sleeve 111 using any suitable technique. For example, the second polymer may be applied by dipping, brushing, spraying, etc. A thickness of the intermediate layer 112 may range from about 40 μm to about 350 μm, from about 100 μm to about 250 μm and be about 200 μm. In some embodiments, the intermediate layer 112 may also include additives. For example, the additives may be radiopaque agents, antimicrobial agents, antithrombogenic agents, etc.

In certain embodiments, a first bond 125 between the inner sleeve 111 and the intermediate layer 112 may form when the second polymer of the intermediate layer 112 is applied to the inner sleeve 111. The first bond 125 may include adhesive forces such as chemical (e.g., ionic, covalent, or hydrogen bonds), mechanical, or dispersive (e.g., van der Waals forces). In some embodiments, the materials of the inner sleeve 111 and the intermediate layer 112 may be selected such that they are configured to adhere to each other. For example, an inner sleeve 111 comprised of extruded silicone may tend to adhere to a sprayed layer of softer silicone.

The tie layer 113 may be disposed over the intermediate layer 112 such that the tie layer 113 covers a full length of the intermediate layer 112. The tie layer 113 may include a third polymer that is different than the polymers of the inner sleeve 111 and the intermediate layer 112. The third polymer and the first and second polymers may also comprise different formulations of similar materials, such as three types of silicone with different hardnesses or other properties. Thus, in certain embodiments, the third polymer of the tie layer 113 may be silicone. In other embodiments, the third polymer of the tie layer 113 may be any suitable material, such as polyurethane, fluoroelastomer, thermal plastic elastomer, etc. The third polymer may have a hardness that is less than the hardness of the second polymer of the intermediate layer 112. A hardness of the third polymer of the tie layer 113 may range from about 5 A to about 80 A, from about 10 A to about 25 A, and may be about 15 A on a Shore A hardness scale. A thickness of the tie layer 113 may range from about 1 µm to about 400 µm, from about 5 µm to about 50 µm, and be about 10 µm. In some embodiments, the tie layer 113 may also include additives. For example, the additives may be radiopaque agents, antimicrobial agents, antithrombogenic agents, etc.

In certain embodiments, a second bond 127 between the intermediate layer 112 and the tie layer 113 may form when the third polymer of the tie layer 113 is applied to the intermediate layer 112. The second bond 127 may include adhesive forces such as chemical (e.g., ionic, covalent, or hydrogen bonds), mechanical, or dispersive (e.g., van der Waals forces). As with the inner sleeve 111 and intermediate layer 112, in embodiments wherein the tie layer 113 comprises a silicone and the intermediate layer 112 comprises a silicone, the layers may be configured to adhere to each other as the tie layer 113 is applied to the intermediate layer 112.

The outer sleeve 114 may be disposed over the tie layer 113 such that the outer sleeve 114 covers a full length of the intermediate layer 112. The outer sleeve 114 may be porous and comprise a plurality of pores. A fourth polymer of the outer sleeve 114 may include PTFE. In other embodiments, the outer sleeve 114 may include any suitable material, such as polyethylene terephthalate, poly amide, polyurethane, etc. The outer sleeve 114 may include expanded PTFE having a plurality pores formed by fibrils connected at nodes. The pores may be sized to permit ingrowth of tissue into the outer sleeve 114. For example, an internodal distance may range from about 5 µm to about 80 µm, from about 15 µm to about 25 µm, and from about 17 µm to about 20 µm. In certain embodiments, the outer sleeve 114 may include rotational spun or electrospun PTFE fibers with pores disposed between the fibers. The pores may be sized to permit ingrowth of tissue into the outer sleeve 114.

In certain embodiments, the tie layer 113 and the outer sleeve 114 may form a laminate when coupled together, meaning the materials of the tie layer 113 and the materials of outer sleeve 114 may be blended along a coupling zone. The third polymer of the tie layer 113 may flow into the pores of the outer sleeve 114 to form a mechanical bond 128. Stated another way, the boundary between the tie layer 113 and the outer sleeve 114 may comprise a zone wherein the material of the tie layer 113 permeates into the material of the outer sleeve 114. A depth of the coupling zone may range from about 1 µm to about 20 µm. Breakage of the mechanical bond 128 to separate the tie layer 113 from the outer sleeve 114 may result in destruction of interfacing portions of both the tie layer 113 and the outer sleeve 114.

In certain therapies, the vascular graft 100 may be utilized to treat a patient with hemodialysis. The vascular graft 100 may be implanted into a patient. One end of the body 110 may be coupled to an artery and the opposite end may be coupled to a vein such that the bore 118 is in fluid communication with the patient's vasculature and blood can flow through the bore 118. The wall 119 of the body 110 may be punctured with a first vascular access device (e.g., needle) such that the first needle forms a puncture site in the wall 119. The first needle may be in fluid communication with the bore 118. In some embodiments, the body 110 may be punctured by a second needle to form a second puncture site. Blood may be withdrawn from the bore 118 through the first needle and returned to the bore 118 through the second needle following filtration. Following treatment, the first and second needles may be removed from the body 110. The first and second puncture sites may be closed and sealed due to the elasticity of at least one of the layers 111, 112, 113, 114 of the wall 119 of the body 110. Such treatments may be repeated multiple times over an extended time period.

Figure 3:
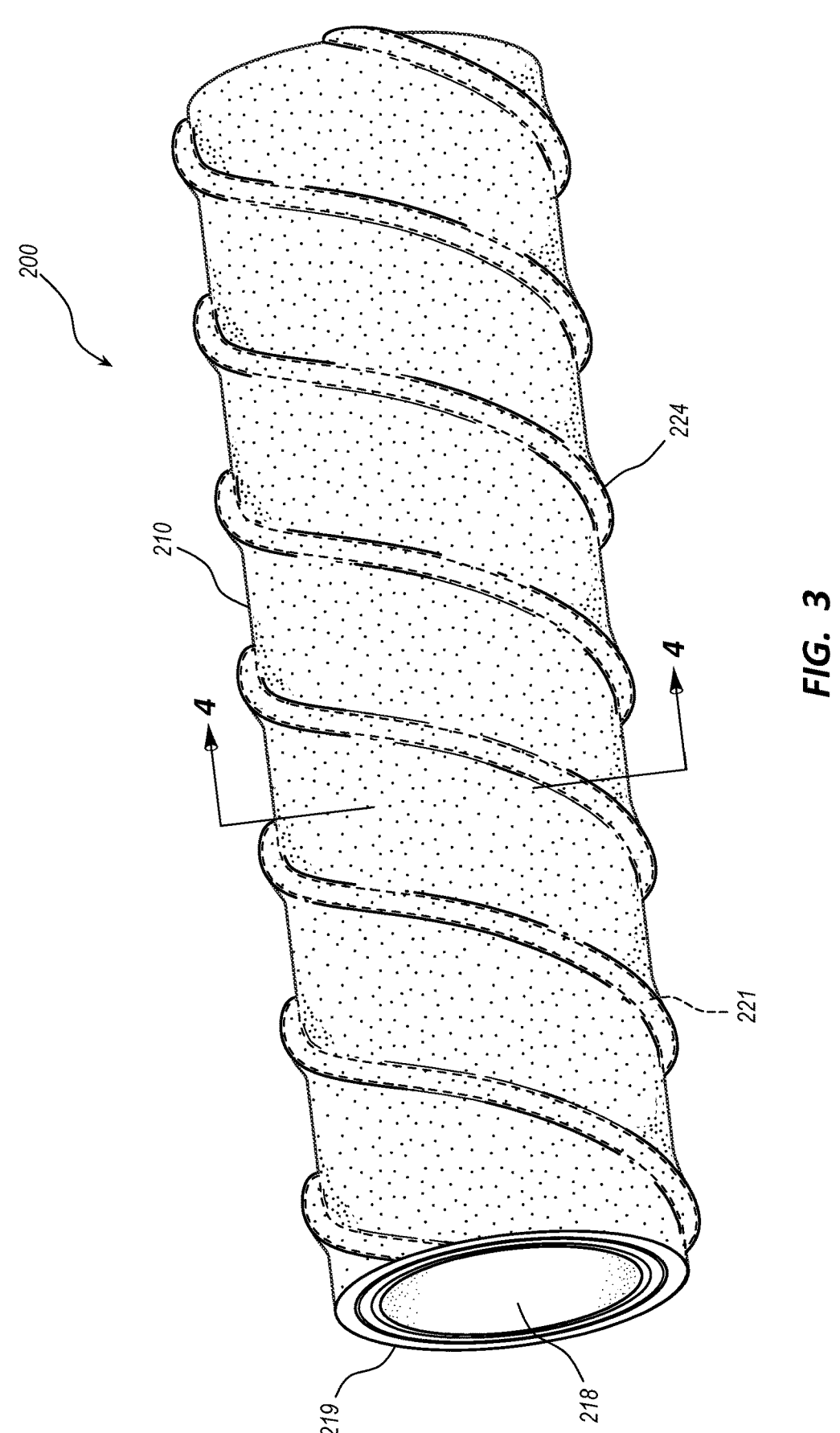
FIG. 3 is a perspective view of another embodiment of a vascular graft.
Figure 4:
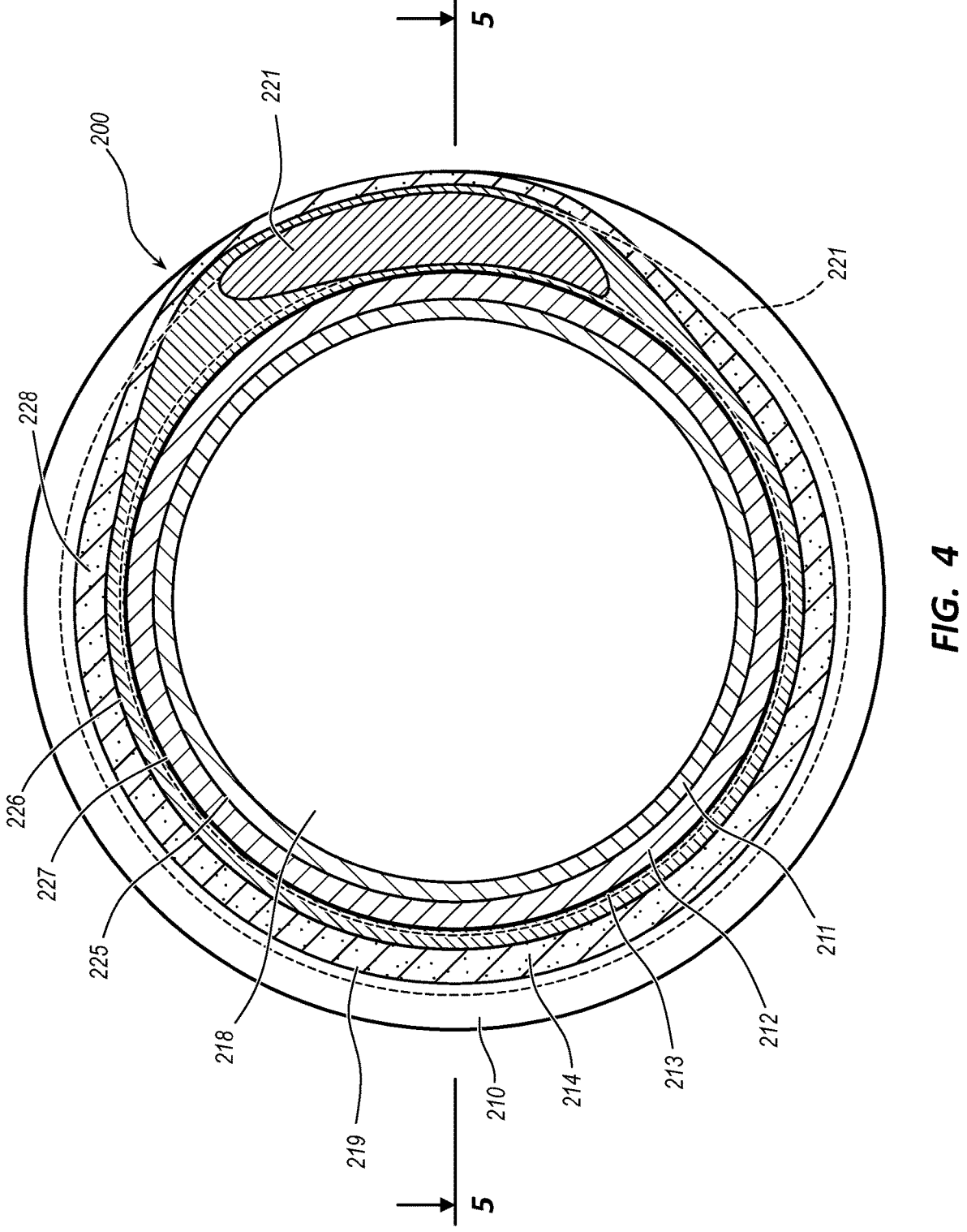
FIG. 4 is a transverse cross-sectional view of the vascular graft of FIG. 3, taken through plane 4-4 of FIG. 3.
Figure 5:
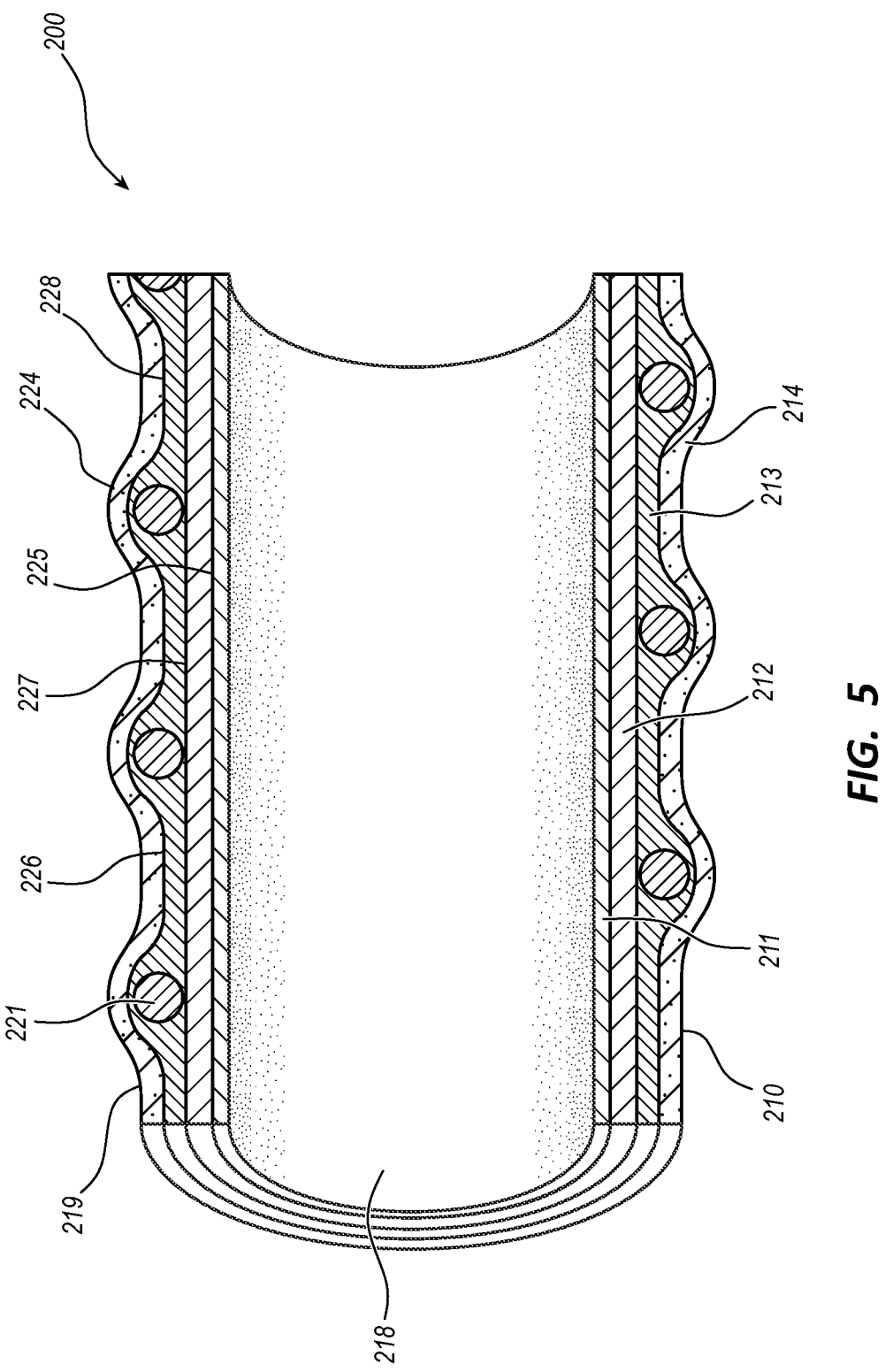
FIG. 5 is an axial cross-sectional view of the vascular graft of FIG. 3, taken through plane 5-5 of FIG. 4.

FIGS. 3-5 depict an embodiment of a vascular graft 200 that resembles the vascular graft 100 described above in certain respects. Accordingly, like features are designated with like reference numerals, with the leading digit incremented to "2." For example, the embodiment depicted in FIGS. 3-5 includes a body 210 that may, in some respects, resemble the body 110 of FIGS. 1-2. Relevant disclosure set forth above regarding similarly identified features thus may not be repeated hereafter. Moreover, specific features of the body 110 and related components shown in FIGS. 1-2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the vascular graft 200 and related components depicted in FIGS. 3-5. Any suitable combination of the features, and variations of the same, described with respect to the vascular graft 100 and related components illustrated in FIGS. 1-2 can be employed with the vascular graft 200 and related components of FIGS. 3-5, and vice versa. This pattern of disclosure applies equally to further embodiments depicted in subsequent figures and described hereafter, wherein the leading digits may be further incremented.

FIGS. 3-5 depict an embodiment of a vascular graft 200. As depicted, the vascular graft 200 may include a body 210. The body 210 may include a tubular form having a wall 219 and a bore 218. A transverse cross-section of the body 210 may be circular or annular shaped as shown in FIG. 4. In other embodiments, the transverse cross-section of the body 210 may be of any suitable shape, such as an oval, lens, semicircle, ellipse, etc. The bore 218 may extend through a length of the body 210. In some embodiments, an end of the body 210 may be tapered such that a bore diameter is smaller adjacent an end of the body 210 than a bore diameter adjacent a medial portion of the body 210. Embodiments wherein both the proximal and distal ends are tapered, only one end is tapered, and embodiment wherein neither end is tapered are within the scope of this disclosure.

The wall 219 may be formed of multiple layers. Any of the layers may be comprised of one or more sublayers of material. In the illustrated embodiment of FIG. 4, the wall 219 comprises four layers. As depicted, the wall 219 includes an inner layer or sleeve 211, an intermediate layer 212, a tie layer 213, an outer layer or sleeve 214, and a bead 221.

In some embodiments, the inner sleeve 211, the intermediate layer 212, the tie layer 213, and the outer sleeve 214 are analogous to the inner sleeve 111, intermediate layer 112, tie layer 113, and outer sleeve 114 of the embodiment of FIGS. 1-2. Any disclosure recited in connection with those layers 111, 112, 113, and 114 analogously applies to the layers 211, 212, 213, and 214 of the embodiment of FIGS. 3-5. As compared to the embodiment of FIGS. 1-2, the embodiment of FIGS. 3-5 also comprises a bead 221 as further detailed below.

The inner sleeve 211 may be an extruded tube. The inner sleeve 211 may be formed from any suitable material that may provide durability and support during manufacture of the vascular graft 200. For example, the inner sleeve 211 may include a first polymer, including silicone. In certain other embodiments, the inner sleeve 211 may include a fibrous PTFE film. As with previous embodiments, in some embodiments, the inner sleeve 211 may comprise an extruded silicone tube with a fibrous PTFE sublayer coupled to the insider diameter thereof. A hardness of the inner sleeve 211 may range from about 5 A to about 80 A, from about 40 A to about 60 A, and may be about 50 A on a Shore A hardness scale. A thickness of the inner sleeve 211 may range from about 40 μm to about 350 μm, from about 100 μm to about 250 μm, and be about 200 μm. The inner sleeve 211 may be configured as the innermost layer of the wall and, thus, may be configured as the blood contacting layer of the vascular graft 200.

The intermediate layer 212 may be disposed over the inner sleeve 211 such that the intermediate layer 212 covers a full length of the inner sleeve 211. The intermediate layer 212 may include a second polymer that is different than the first polymer of the inner sleeve 211. The second polymer of the intermediate layer 212 may be silicone. The second polymer may have a hardness that is less than the hardness of the first silicone polymer of the inner sleeve 211. A hardness of the second polymer of the intermediate layer 212 may range from about 5 A to about 80 A, from about 15 A to about 40 A, and may be about 25 A on a Shore A hardness scale. The second polymer may be applied to the inner sleeve 211 using a spraying technique where a dispersion of the second polymer and a solvent is aerosolized or atomized. A thickness of the intermediate layer 212 may range from about 40 μm to about 350 μm, from about 100 μm to about 250 μm, and be about 200 μm.

In certain embodiments, a first bond 225 between the inner sleeve 211 and the intermediate layer 212 may form when the second polymer of the intermediate layer 212 is applied to the inner sleeve 211. The first bond 225 may include adhesive forces such as chemical (e.g., ionic, covalent, or hydrogen bonds), mechanical, or dispersive (e.g., van der Waals forces).

The tie layer 213 may be disposed over the intermediate layer 212 such that the tie layer 213 covers a full length of the intermediate layer 212. The tie layer 213 may include a third polymer that is different than the polymers of the inner sleeve 211 and the intermediate layer 212. The third polymer of the tie layer 213 may be silicone. The third polymer may have a hardness that is less than the hardness of the second polymer of the intermediate layer 212. A hardness of the third polymer of the tie layer 213 may range from about 5

A to about 80 A, from about 10 A to about 25 A, and may be about 15 A on a Shore A hardness scale.

In certain embodiments, a second bond 227 between the intermediate layer 212 and the tie layer 213 may form when the third polymer of the tie layer 213 is applied to the intermediate layer 212. The second bond 227 may include adhesive forces such as chemical (e.g., ionic, covalent, or hydrogen bonds), mechanical, or dispersive (e.g., van der Waals forces).

As illustrated in the embodiment of FIGS. 3-5, the bead 221 may be disposed within the tie layer 213 between the intermediate layer 212 and the outer sleeve 214. The bead 221 may be configured to provide reinforcement to the vascular graft 200 to prevent kinking and/or collapsing. Embodiments where the wall 219 comprises a single layer or multiple layers are within the scope of this disclosure. As depicted, the bead 221 extends spirally about a longitudinal axis of the body 210 over the length of the body 210 to increase a kink resistance of the body 210. In other embodiments, the bead 221 may extend only along longitudinal portions of the body 210. For example, in certain embodiments the bead 221 may be disposed along a medial portion of the body 210 and not around end portions of the body 210. Such a configuration may be configured to facilitate suturing of the ends of the body 210 to a patient's blood vessels without the suture directly interacting with the bead 221. The bead 221 may include a plurality of spiral winds where each wind is spaced from an adjacent wind an equidistance ranging from about 1 mm to about 10 mm. In other embodiments, the distance between winds may be variable over the length of the body 210 to provide variable kink resistance and accessibility to the bore 218 with a needle. The bead 221 may be formed of fluorinated ethylene propylene. In certain other embodiments, the bead 221 may include any suitable material, such as stainless steel, titanium, nickel-titanium alloy, polyurethane, densified expanded PTFE, high durometer silicone, polypropylene, polyether block amide, etc. A transverse cross-sectional shape of the bead 221 may be circular, D-shaped, ribbon shaped, etc. A diameter of the bead 221 may range from about 0.01 mm to about 1.5 mm.

In certain embodiments, the bead 221 may be formed from densified areas of the outer sleeve 214. For example, the bead 221 may include discrete rings, a longitudinally extending spiral bead, or discrete C-shaped beads of densified expanded PTFE. The densified expanded PTFE bead may be formed by selectively applying a compressive force and heat to the bead area to compress or densify the expanded PTFE and eliminate the pores. A tensile force may be applied to the outer sleeve to return the expanded PTFE to an expanded state.

As depicted, the third polymer of the tie layer 213 may surround the bead 221 such that the bead 221 is encapsulated within the tie layer 213. The bead 221 may increase an outer diameter of the body 210 in areas adjacent the bead 221, as compared to portions where the bead 221 is not present. In other words, the outer diameter may be larger in areas over the bead 221 than in areas between the winds of the bead 221 such that bumps 224 may be formed at an exterior surface of the body 210. Additionally, a thickness of the wall 219 may be larger adjacent the bead 221 than between the winds of the bead 221.

The outer sleeve 214 may be disposed over the tie layer 213 such that the outer sleeve 214 covers a full length of the intermediate layer 212. The outer sleeve 214 may be porous and comprise a plurality of pores. A fourth polymer of the outer sleeve 214 may include PTFE. The outer sleeve 214 may comprise expanded PTFE having a plurality pores formed by fibrils connected at nodes or may comprise rotational spun or electrospun PTFE fibers with pores disposed between the fibers.

In certain embodiments, the tie layer 213 and the outer sleeve 214 may form a laminate when coupled together. The third polymer of the tie layer 213 may flow into the pores of the outer sleeve 214 to form a mechanical bond 228. Breakage of the mechanical bond 228 to separate the tie layer 213 from the outer sleeve 214 may result in destruction of interfacing portions of both the tie layer 213 and the outer sleeve 214.

Figure 6:
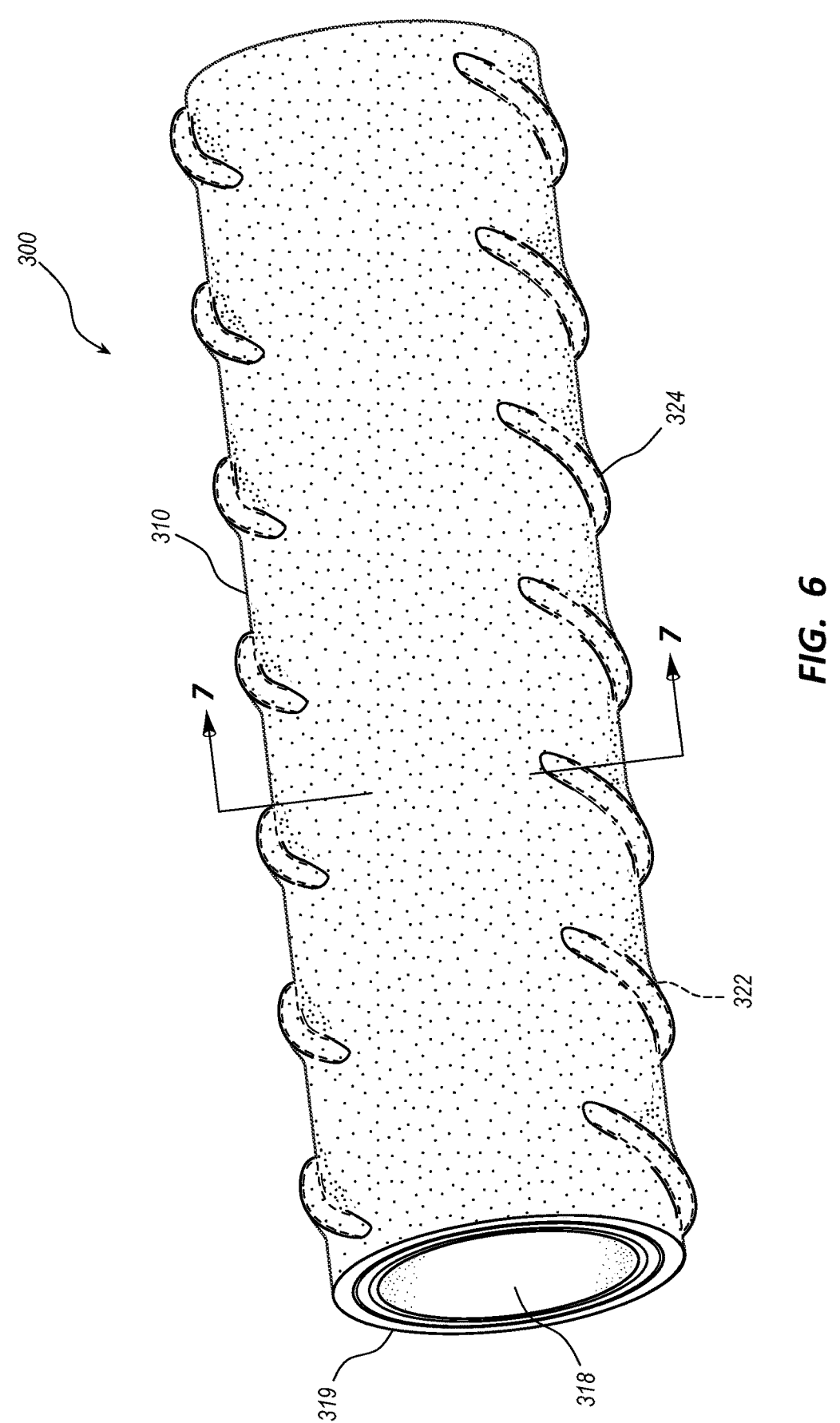
FIG. 6 is a perspective view of another embodiment of a vascular graft.
Figure 7:
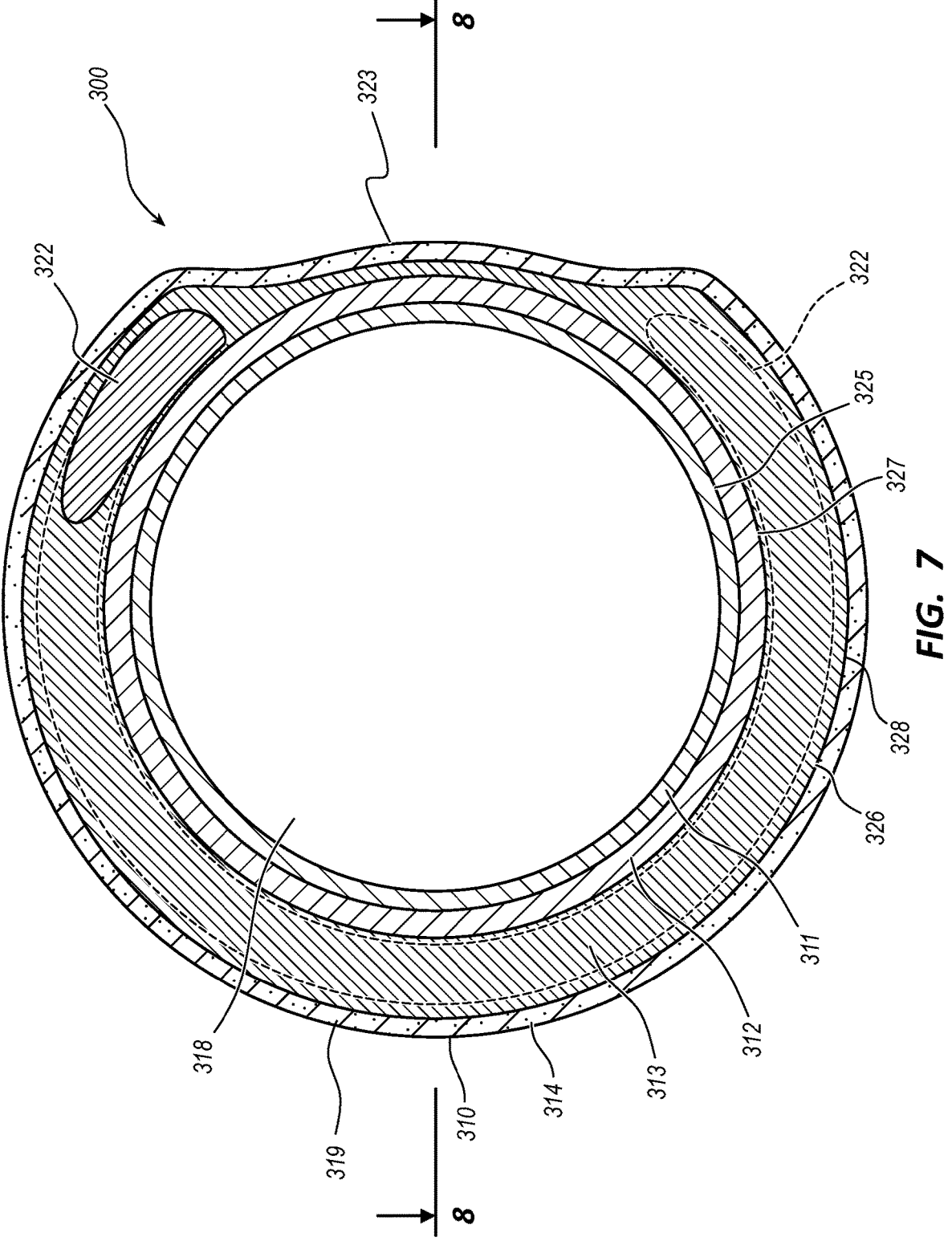
FIG. 7 is a transverse cross-sectional view of the vascular graft of FIG. 6, taken through plane 7-7 of FIG. 6.
Figure 8:
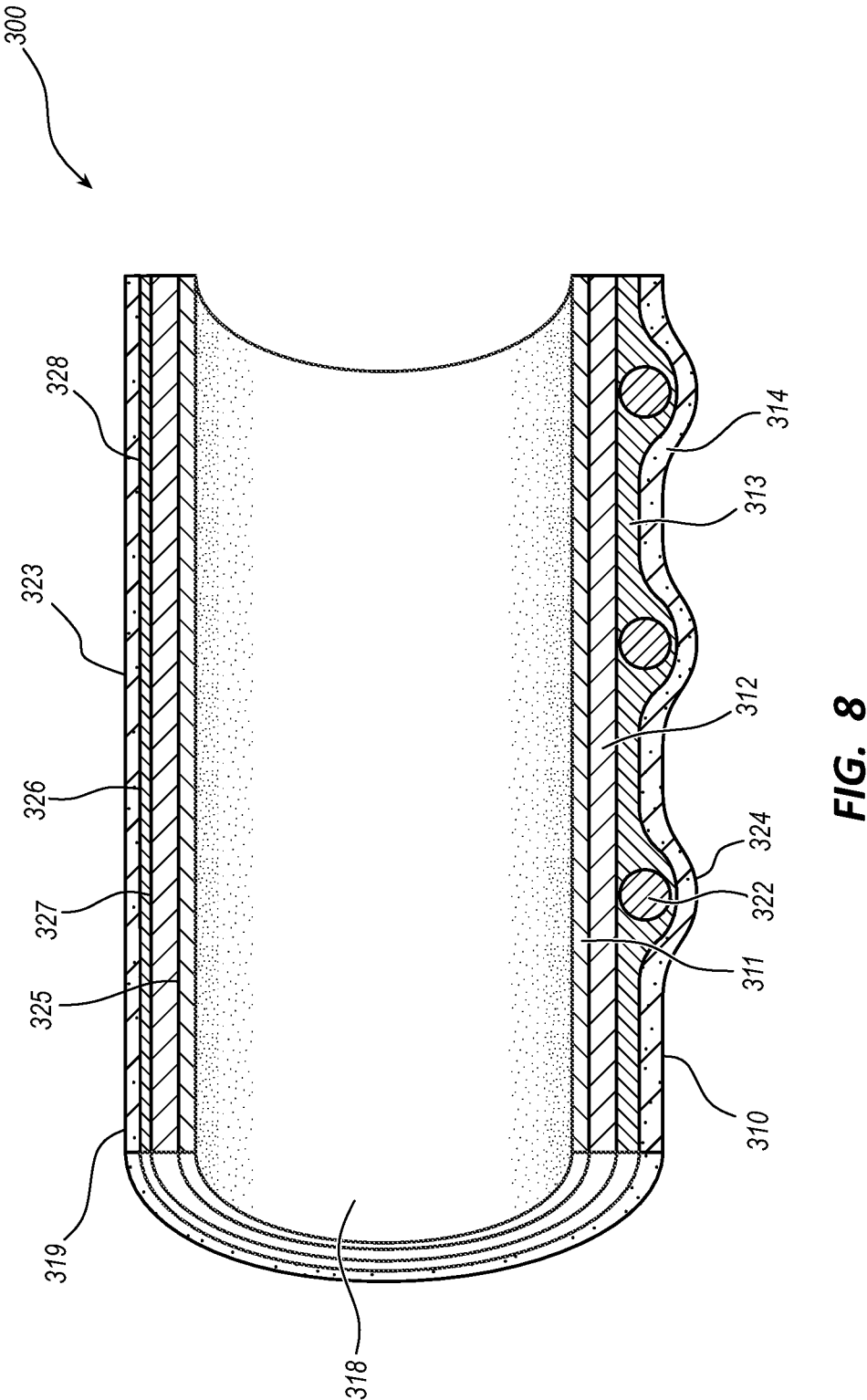
FIG. 8 is an axial cross-sectional view of the vascular graft of FIG. 6, taken through plane 8-8 of FIG. 7.

FIGS. 6-8 depict an embodiment of a vascular graft 300. As depicted, the vascular graft 300 may include a body 310. The body 310 may include a tubular form having a wall 319 and a bore 318. A transverse cross-section of the body 310 may be circular or annulus shaped as shown in FIG. 7. The bore 318 may extend through a length of the body 310. In some embodiments, an end of the body 310 may be tapered such that a bore diameter is smaller adjacent an end of the body 310 than a bore diameter adjacent a medial portion of the body 310. As with the other embodiments disclosed herein, the embodiment of FIGS. 6-8 may have different cross sectional profiles and may have only one, or both, ends tapered.

The wall 319 may be formed of multiple layers. In the illustrated embodiment of FIG. 7, the wall 319 includes four layers. As depicted, the wall 319 includes an inner layer or sleeve 311, an intermediate layer 312, a tie layer 313, an outer layer or sleeve 314, and a plurality of beads 322. Disclosure related above in connection with the inner sleeves 111, 211, intermediate layers 112, 212, tie layers 113, 213, outer sleeve 314, and bead 222 analogously applies to the inner sleeve 311, the intermediate layer 312, the tie layer 313, the outer layer 314, and the beads 322.

The inner sleeve 311 may be an extruded tube. The inner sleeve 311 may be formed from any suitable material that may provide durability and support during manufacture of the vascular graft 300. For example, the inner sleeve 311 may include a first polymer, including silicone. In certain other embodiments, the inner sleeve 311 may include a fibrous PTFE film, including embodiments wherein the inner sleeve 311 comprises an extruded silicone layer with a fibrous PTFE film coupled to its inside diameter. A hardness of the first polymer may range from about 5 A to about 80 A, from about 40 A to about 60 A, and may be about 50 A on a Shore A hardness scale. A thickness of the inner sleeve 311 may range from about 40 μm to about 350 μm, from about 100 μm to about 250 μm and be about 200 μm.

The intermediate layer 312 may be disposed over the inner sleeve 311 such that the intermediate layer 312 covers a full length of the inner sleeve 311. The intermediate layer 312 may include a second polymer that is different than the first polymer of the inner sleeve 311. The second polymer of the intermediate layer 312 may be silicone. The second polymer may have a hardness that is less than the hardness of the first silicone polymer of the inner sleeve 311. A hardness of the second polymer of the intermediate layer 312 may range from about 5 A to about 80 A, from about 15 A to about 40 A, and may be about 25 A on a Shore A hardness scale. The second polymer may be applied to the inner sleeve 311 using a spraying technique where a dispersion of the second polymer and a solvent is aerosolized or atomized. A thickness of the intermediate layer 312 may range from about 40 μm to about 350 μm, from about 100 μm to about 250 μm, and be about 200 μm.

In certain embodiments, a first bond 325 between the inner sleeve 311 and the intermediate layer 312 may form when the second polymer of the intermediate layer 312 is applied to the inner sleeve 311. The first bond 325 may include adhesive forces such as chemical (e.g., ionic, covalent, or hydrogen bonds), mechanical, or dispersive (e.g., van der Waals forces).

The tie layer 313 may be disposed over the intermediate layer 312 such that the tie layer 313 covers a full length of the intermediate layer 312. The tie layer 313 may include a third polymer that is different than the polymers of the inner sleeve 311 and the intermediate layer 312. The third polymer of the tie layer 313 may be silicone. The third polymer may have a hardness that is less than the hardness of the second polymer of the intermediate layer 312. In other embodiments, the third polymer may have a hardness that is greater than the hardness of the second polymer. A hardness of the third polymer of the tie layer 313 may range from about 5 A to about 80 A, from about 10 A to about 25 A and may be about 15 A on a Shore A hardness scale.

In certain embodiments, a second bond 327 between the intermediate layer 312 and the tie layer 313 may form when the third polymer of the tie layer 313 is applied to the intermediate layer 312. The second bond 327 may include adhesive forces such as chemical (e.g., ionic, covalent, or hydrogen bonds), mechanical, or dispersive (e.g., van der Waals forces).

As illustrated in the embodiment of FIGS. 6-8, the beads 322 are disposed within the tie layer 313 between the intermediate layer 312 and the outer sleeve 314. As depicted, each of the beads 322 is generally C-shaped and configured to surround a portion of a circumference of the body 310. The beads 322 may be disposed over a length of the body 310. In other embodiments, the beads 322 may be disposed around portions of the body 310. For example, in certain embodiments the beads 322 may be disposed around a medial portion of the body 310 and not around end portions of the body 310. This configuration facilitates suturing of the ends of the body 310 to a patient's blood vessels without the suture directly interacting with the beads 322.

In the embodiment of FIGS. 6-8, the beads 322 extend only around a partial circumference of the vascular graft 300. For example, in the illustrated embodiment, the beads 322 follow on overall spiral or helical path, however the path is discontinuous, such that it comprises spaces along the helical path. As shown in FIG. 6, these spaces may be aligned at a circumferential position along a length of the vascular graft 300, creating a gap running longitudinally along a portion of the length of the vascular graft. In other instances, the beads 322 may be comprised of partial circular members where each bead is at the same longitudinal position on the body 310, rather than following a helical path. The partial circular members may be spaced along at least a portion of the length of the body. The partial circular members may be positioned such they define a gap disposed between ends of the partial circular members. Thus, the gap may be positioned at a particular circumferential position and extend along a longitudinal length of the vascular graft 300. Disclosure recited herein in connection with C-shaped beads that extend only around a portion of a circumference of the body 310 applies to both beads disposed along a discontinuous path and partial circular beads where each bead is positioned at a constant longitudinal position around its circumference.

The beads 322 may be disposed an equidistance apart ranging from about 1 mm to about 10 mm. In other embodiments, the distance between each bead 322 may be variable over the length of the body 310 to provide variable kink resistance. The wall 319 includes a gap 323 between ends of the C-shaped beads 322. The gap 323 may be longitudinal aligned over the length of the body 310. Each of the beads 322 may surround from about 50% to about 80%, from about 55% to about 75%, and from about 60% to about 70% of the body 310. In other words, a length of an arc of the gap 323 may be from about 20% to about 50% of a circumference of the body 310. In some embodiments, a visually observable indicium (e.g., line) printed on the outer sleeve 314 may mark the gap 323 to facilitate proper orientation of the vascular graft 300 during implantation. When the vascular graft 300 is implanted, the indicium may be observable via visualization techniques, such as fluoroscopy and ultrasound. The bead 322 may be formed of fluorinated ethylene propylene (FEP). In certain other embodiments, the bead 322 may include any suitable material, such as stainless steel, titanium, nickel-titanium alloy, polyurethane, densified expanded PTFE, high durometer silicone, polypropylene, polyether amide, etc. A transverse cross-sectional shape of the bead 322 may be circular, D-shaped, ribbon shaped, etc. A diameter of the bead 322 may range from about 0.01 mm to about 1.5 mm.

As depicted, the third polymer of the tie layer 313 may surround the beads 322 such that the beads 322 are encapsulated within the tie layer 313. The beads 322 may increase an outer diameter of the body 310 in areas adjacent the beads 322. In other words, the outer diameter may be larger in areas over the beads 322 than in areas between the beads 322 such that bumps 324 may be formed at an exterior surface of the body 310. Additionally, a thickness of the tie layer 313 may be larger between the beads 322 than adjacent the gap 323 as illustrated in FIG. 8.

The outer sleeve 314 may be disposed over the tie layer 313 such that the outer sleeve 314 covers a full length of the intermediate layer 312. The outer sleeve 314 may be porous and comprise a plurality of pores. A fourth polymer of the outer sleeve 314 may include PTFE. The outer sleeve 314 may include expanded PTFE having a plurality pores formed by fibrils connected at nodes.

In certain embodiments, the tie layer 313 and the outer sleeve 314 may form a laminate when coupled together. The third polymer of the tie layer 313 may flow into the pores of the outer sleeve 314 to form a mechanical bond 328. Breakage of the mechanical bond 228 to separate the tie layer 213 from the outer sleeve 214 may result in destruction of interfacing portions of both the tie layer 213 and the outer sleeve 214.

In use, the vascular graft 300 may be utilized to treat a patient with hemodialysis. The wall 319 of the body 310 may be punctured with one or two needles such that one or two puncture sites are formed in the wall 319. The needles may puncture the wall 319 adjacent the gap 323 and be advanced into the bore 318. The clinician may feel a first insertion resistance as the needles puncture the wall 319 adjacent the gap 323 and then a loss of resistance as the needles are advanced into the bore 318. This loss of resistance may provide a confirmation to the clinician of proper placement of the needles within the bore 318. Further advancement of the needles through the bore 318 may result in the puncture of a back wall of the body 310. As the back wall is punctured, the clinician may feel a second insertion resistance that may be greater than the first insertion resistance. The increased second insertion resistance may be caused by the increase in thickness of the tie layer 312 between the beads 322 as previously discussed.

Blood may be withdrawn from the bore 318 through one of the needles and returned to the bore 118 through the other needle following filtration. Following treatment, the needles may be removed from the vascular graft 300. The puncture sites may be closed and sealed due to the elasticity of at least one of the layers 311, 312, 313, 314 of the wall 319 of the body 310.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "about." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:
1. A vascular graft, comprising:
an inner sleeve comprising a first polymer;
an intermediate layer comprising a second polymer;
a tie layer comprising a third polymer; and
a porous outer sleeve;

wherein the intermediate layer is disposed between the inner sleeve and the tie layer and the tie layer is disposed between the intermediate layer and the porous outer sleeve;

wherein the first polymer is different than the second polymer;

wherein a hardness of the first polymer is harder than a hardness of the second polymer;

wherein a hardness of the third polymer is harder less than that the hardness of the second polymer;

wherein the tie layer forms a mechanical bond with the porous outer sleeve;

wherein the mechanical bond between the tie layer and the porous outer layer form a boundary in which the tie layer permeates into pores of the outer layer; and wherein a material of the tie layer permeates into a material of the outer sleeve, such that a coupling zone of the mechanical bond comprises a depth between 1 μm to 20 μm.

2. The vascular graft of claim 1, wherein the first polymer comprises any one of a silicone, a polyurethane, and a fluoroelastomer with a hardness from SA to 80 A on the Shore A hardness scale.

3. The vascular graft of claim 1, wherein the inner sleeve comprises any one of expanded polytetrafluoroethylene (PTFE), rotational spun PTFE, and electrospun PTFE.

4. The vascular graft of claim 1, wherein the second polymer comprises any one of a silicone, a polyurethane, and a fluoroelastomer with a hardness from SA to 80 A on the Shore A hardness scale.

5. The vascular graft of claim 1, wherein the intermediate layer is a sprayed layer.

6. The vascular graft of claim 1, wherein the third polymer comprises any one of a silicone, a polyurethane, and a fluoroelastomer with a hardness from SA to 80 A on the Shore A hardness scale.

7. The vascular graft of claim 1, wherein the porous outer sleeve comprises any one of expanded PTFE, rotational spun PTFE, electrospun PTFE, polyethylene terephthalate, polyurethane, polyurethane, and polyamide.

8. The vascular graft of claim 1, wherein a first bond is disposed between the inner sleeve and the intermediate layer and a second bond is disposed between the intermediate layer and the tie layer.

9. The vascular graft claim 1, further comprising a bead disposed within the tie layer.

10. The vascular graft of claim 9, wherein the bead comprises any one of stainless steel, titanium, nickel-titanium alloy, fluorinated ethylene propylene, densified expanded polytetrafluoroethylene, high durometer silicone, polypropylene, polyether block amide, and polyurethane.

11. The vascular graft of claim 10, wherein the bead helically extends along at least a portion of the vascular graft.

12. The vascular graft of claim 10, wherein the bead comprises a plurality of C-shaped members, wherein a first end of each C-shaped member is directed toward a first end of the vascular graft, wherein a second end of each C-shaped member is directed toward a second end of the vascular graft, and wherein the first end and the second end of the vascular graft arc disposed on opposite longitudinal ends of the vascular graft.

13. The vascular graft of claim 12, further comprising a gap disposed between opposing ends of each of the plurality of C-shaped members, wherein a thickness of a graft wall adjacent the gap is less than a thickness of a graft wall at a position opposite of the gap.

14. The vascular graft of claim 1, wherein the first polymer comprises a hardness from 40 A to 60 A on the Shore A hardness scale, wherein the second polymer comprises a hardness from 15 A to 40 A on the Shore A hardness scale, and wherein the third polymer comprises a hardness from 10 A to 25 A on the Shore A hardness scale.

15. The vascular graft of claim 1, wherein the first polymer comprises a hardness of about 50 A on the Shore A hardness scale, the second polymer comprises a hardness of about 25 A on the Shore A hardness scale, and the third polymer comprises a hardness of about 15 A on the Shore A hardness scale.

16. The vascular graft of claim 1, wherein the first polymer is silicone with a first hardness, the second polymer is silicone with a second hardness, and the third polymer is silicone with a third hardness, wherein the first hardness is greater than the hardness of the second hardness and the third hardness, wherein the second hardness is greater than the hardness of the third hardness but less than the hardness of the first hardness, and wherein the third hardness is less than the hardness of the first hardness and the second hardness.

17. The vascular graft of claim 16, wherein the first hardness is between 40 A to 60 A on the Shore A hardness scale, wherein the second hardness is between 15 A to 40 A on the Shore A hardness scale, and wherein the third hardness is between 10 A to 25 A on the Shore A hardness scale.

18. The vascular graft of claim 16, wherein the first hardness is about 50 A on the Shore A hardness scale, the second hardness is about 25 A on the Shore A hardness scale, and the third hardness is about 15 A on the Shore A hardness scale.

* * * * *